United States Patent
Li

(10) Patent No.: US 9,863,941 B2
(45) Date of Patent: Jan. 9, 2018

(54) MICROCHIP AND METHOD FOR DETECTING MOLECULES AND MOLECULAR INTERACTIONS

(75) Inventor: Changming Li, Singapore (SG)

(73) Assignee: Nanyang Technological University, Singapore (SG)

( * ) Notice: Subject to any disclaimer, the term of this patent is extended or adjusted under 35 U.S.C. 154(b) by 1137 days.

(21) Appl. No.: 11/547,405

(22) PCT Filed: Apr. 1, 2005

(86) PCT No.: PCT/SG2005/000112
§ 371 (c)(1),
(2), (4) Date: Oct. 2, 2006

(87) PCT Pub. No.: WO2005/095262
PCT Pub. Date: Oct. 13, 2005

(65) Prior Publication Data
US 2008/0108095 A1     May 8, 2008

Related U.S. Application Data

(60) Provisional application No. 60/558,116, filed on Apr. 1, 2004, provisional application No. 60/558,118, filed on Apr. 1, 2004.

(51) Int. Cl.
*G01N 33/543* (2006.01)
*B01L 3/00* (2006.01)

(52) U.S. Cl.
CPC .. *G01N 33/54366* (2013.01); *B01L 3/502746* (2013.01); *G01N 33/5438* (2013.01); *B01L 2200/027* (2013.01); *B01L 2200/141* (2013.01); *B01L 2300/0636* (2013.01); *B01L 2300/0645* (2013.01); *B01L 2300/0816* (2013.01); *B01L 2300/0851* (2013.01); *B01L 2300/0864* (2013.01); *B01L 2300/0867* (2013.01); *B01L 2300/0874* (2013.01); *B01L 2400/0457* (2013.01); *B01L 2400/0487* (2013.01)

(58) Field of Classification Search
None
See application file for complete search history.

(56) References Cited

U.S. PATENT DOCUMENTS

| 4,468,680 | A | * | 8/1984 | Martner | 347/68 |
| 5,607,475 | A | * | 3/1997 | Cahalan et al. | 424/423 |
| 5,772,877 | A | * | 6/1998 | Dvorchik et al. | 210/223 |
| 6,074,827 | A | * | 6/2000 | Nelson et al. | 435/6 |
| 6,632,655 | B1 | * | 10/2003 | Mehta et al. | 506/14 |
| 2002/0023684 | A1 | * | 2/2002 | Chow | 137/833 |
| 2002/0185183 | A1 | | 12/2002 | O'Connor et al. | |
| 2003/0054355 | A1 | * | 3/2003 | Warthoe | 435/6 |
| 2003/0096405 | A1 | * | 5/2003 | Takayama et al. | 435/366 |
| 2004/0005582 | A1 | * | 1/2004 | Shipwash | 435/6 |
| 2004/0005720 | A1 | * | 1/2004 | Cremer et al. | 436/518 |

FOREIGN PATENT DOCUMENTS

| EP | 1 357 178 A1 | 10/2003 |
| WO | WO 2002/068823 A1 | 9/2002 |
| WO | WO 2003/035229 A2 | 5/2003 |
| WO | WO 2003/052428 A1 | 6/2003 |

OTHER PUBLICATIONS

Wang et al., Surface characterization using chemical force microscopy and the flow performance of modified polydimethylsiloxane for microfluidic device applications, 2003, Electrophoresis 24, pp. 1442-1450.*

* cited by examiner

*Primary Examiner* — Ram R Shukla
*Assistant Examiner* — Ellen J Marcsisin
(74) *Attorney, Agent, or Firm* — Dinsmore & Shohl LLP

(57) ABSTRACT

A microchip with flow-through inlet (104) and outlet (106) channels and test channels (108). The test channels (108) are in fluid communication with the inlet (104) and outlet (106) channels, through inlets (114) and outlets (116) respectively. Each test channel (108) has one test site therein for detection of specific molecules or molecular interactions. The inlet (114) in a test channel (108) is elevated from the outlet (116) of the test channel (108) and the outlet (116) is elevated from a fluid level (124) in the outlet channel (106). Back diffusion from outlet channel (106) to the test channels (108) and from the test channels (108) to the inlet channel (104) can thus be inhibited to reduce or eliminate cross-interference between different test sites. The microchip can be useful as a flow-through high density enzyme immunoassay array device with high-throughput.

20 Claims, 5 Drawing Sheets

MICROCHIP AND METHOD FOR DETECTING MOLECULES AND MOLECULAR INTERACTIONS

CROSS-REFERENCE TO RELATED APPLICATION

This application claims benefit and priority from U.S. provisional patent application No. 60/558,116 filed Apr. 1, 2004 and U.S. provisional patent application No. 60/558,118 filed Apr. 1, 2004, the contents of each of which are incorporated herein by reference.

FIELD OF THE INVENTION

The present invention relates generally to detection of molecules and molecular interactions, and more particularly to microchips and methods for detecting molecules and their interactions.

BACKGROUND

Detection of biomolecules or their interactions has applications in many biological and biochemical industries. For example, it has been widely used for medical diagnostic applications.

Known detection devices of biomolecules and their interactions include microchips or biochips with arrays of addressable test sites thereon. Such devices are powerful analytical tools because hundreds or thousands of unique test sites can be analyzed simultaneously, with high throughput. In a typical conventional microchip, target molecules can be captured and immobilized at different spots on the microchip for detection. Different test sites may be used to detect different target molecules or the same molecules in different samples. Various techniques may be used to detect the target molecules. For example, the target molecules may be detected optically or electrically. Further, biomolecules or biomolecular interactions may be detected by the enzyme immunoassay (EIA) or enzyme-linked immunosorbent assay (ELISA) techniques, with extremely high sensitivity and specificity.

However, conventional microchips suffer certain drawbacks. For example, in known devices the test sites are often immersed in liquid during detection and cross-interference between different test sites can occur due to diffusion of the molecules to be detected from one test site to another. Such cross-interference can lead to false or inaccurate detection results. The molecules to be detected can be either the target molecules or reaction products which are to be detected to indicate the presence of the target molecules.

A known approach to avoid cross-interference due to diffusion is to increase the distance between different test sites, to reduce the effect of diffusion. For example, Ying Ding et al. disclosed a device based on the EIA electrochemical technique (EIA-EC) in "Feasibility studies of simultaneous multianalyte amperometric immunoassay based on spatial resolution", Journal of Pharmaceutical and Biomedical Analysis, (1999), vol. 19, p. 153, the contents of which are incorporated herein by reference. In this detection device, each test site has a working electrode and the distance between two adjacent electrodes is 2.5 mm. This spatial separation is found to be effective for avoiding cross-interference caused by diffusion when the detection measurement is completed within a certain time period after introducing the enzyme substrate. However, such an approach also has some drawbacks. One problem is that only a small number of test sites can be formed on a microchip device when the distance between adjacent electrodes is so large.

An alternative known approach of optical ELISA or EIA is to provide an array of isolated test wells in a chip to avoid cross-interference caused by diffusion. However, these well-based microchips have their own limitations. One problem is that well-density is limited, due to either manufacturing or operation requirements, so that it is difficult to form high-density test sites. Another problem is that a well-based microchip does not allow flow-through operation, thus making automated operation difficult. For example, automated sampling, washing, or dilution on such a chip may require expensive equipments such as robotic devices.

Thus, there remains a need of improved devices and methods for detection of molecules and molecular interactions.

SUMMARY OF THE INVENTION

In summary, a microchip with flow-through inlet and outlet channels and test channels is disclosed. The test channels are in fluid communication with the inlet and outlet channels, through inlets and outlets respectively. Each test channel has one test site therein for detection of specific molecules or molecular interactions. The inlet in a test channel is elevated from the outlet of the test channel and the outlet is elevated from a fluid level in the outlet channel.

Advantageously, back flow or diffusion from the outlet channel to the test channels and from the test channels to the inlet channel can be inhibited to reduce or eliminate cross-interference between different test sites.

Accordingly, an aspect of the present invention relates to a microchip. The microchip comprises a substrate, an inlet channel in the substrate, an outlet channel in the substrate for guiding fluid below a fluid level, and a plurality of test channels in the substrate for guiding fluid flow from the inlet channel to the outlet channel. Each one of the test channels has an inlet for fluid communication with the inlet channel and an outlet for fluid communication with the outlet channel. The inlet is elevated from the outlet for inhibiting back flow through the inlet. The outlet is elevated from the fluid level for inhibiting back flow through the outlet. One test site is in each one of the test channels for detection of a specific molecule or molecular interaction at the test site.

Another aspect of the present invention relates to a method of detecting molecules or molecular interaction. In this method, a microchip is provided. The microchip has a substrate, an inlet channel in the substrate, an outlet channel in the substrate, a plurality of test channels in the substrate each having an inlet for fluid communication with the inlet channel and an outlet for fluid communication with the outlet channel. The inlet is elevated from the outlet. One test site is in each one of the plurality of test channels. A fluid is introduced to the test channels through the inlet channel. Back flow through the inlets and outlets is inhibited by allowing overflow of the fluid from the test channels to the outlet channel through the outlets and maintaining the fluid level in the outlet channel below the outlets, thus inhibiting diffusion of molecules in the fluid from one of the test sites to another one of the test sites. After the fluid has been introduced to the test channels, a molecule or molecular interaction is detected at a test site within the plurality of test sites.

In optical detection, the probe molecules may be directly immobilized on the bottom surface of the detection channel, i.e. detection well; in electronic detection, two (working and counter electrodes) or three electrodes (working, counter and reference electrodes are fabricated in the detection channels, where in all working and counter electrodes can be interconnected respectively for addressable electronic detection.

Other aspects and features of the present invention will become apparent to those of ordinary skill in the art upon review of the following description of specific embodiments of the invention in conjunction with the accompanying Figures.

BRIEF DESCRIPTION OF THE DRAWINGS

In the figures, which illustrate exemplary embodiments of the invention.

DETAILED DESCRIPTION

Figure 1A:
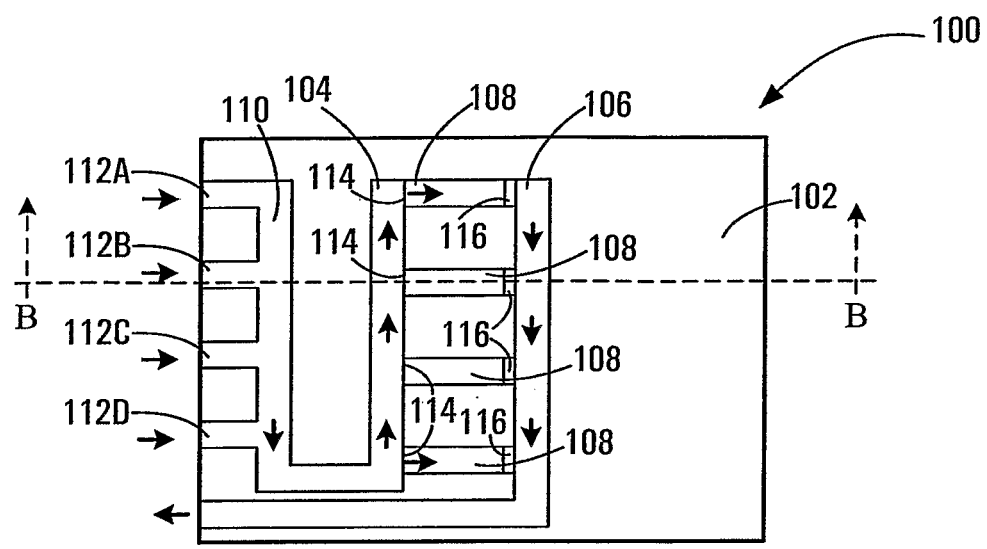
FIG. 1A is a plan view of a microchip, exemplary of an embodiment of the present invention.
Figure 1B:
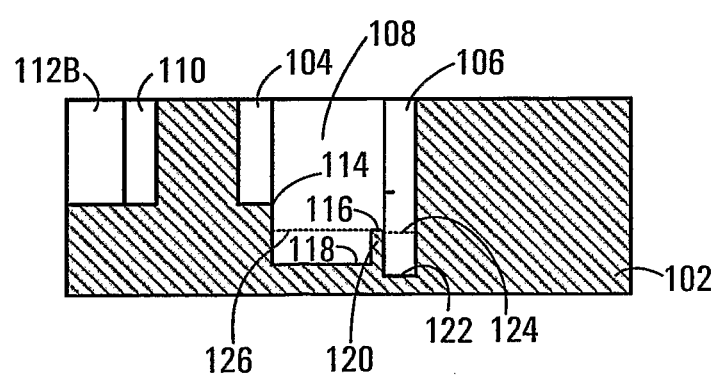
FIG. 1B is a cross-sectional view of the microchip of FIG. 1A taken along the line B-B.

FIGS. 1A and 1B illustrate a microchip or microfluidic biochip 100, exemplary of an embodiment of the present invention.

Biochip 100 includes a substrate 102. An inlet channel 104, an outlet channel 106, and a plurality of test channels 108 are formed in substrate 102. The test channels 108 may be substantially parallel to each other. Inlet channel 104 is in fluid communication with, and can receive fluid from, a dilution channel 110. Dilution channel 110 has multiple inlets 112A to 112D (also collectively and individually referred to as 112), each for introducing or feeding a fluid into dilution channel 110. Each test channel 108 has an inlet 114 and an outlet 116. Each test channel 108 is in fluid communication with inlet channel 104 through inlet 114 and with outlet channel 106 through outlet 116. While four test channels 108 are depicted in FIG. 1A, the number of test channels 108 may vary depending on the particular application and manufacturing considerations. Each test channel 108 has one test site therein for detection of a specific molecule or molecular interaction at the test site, as will be further described below.

As depicted in FIG. 1B, a test channel 108 has a bottom 118 and an overflow wall 120 which forms the lower end of outlet 116. However, as will become apparent, wall 120 is optional and can be omitted. With wall 120, a test well is formed in each channel 108. The well structure may be advantageous in some applications, as will become clear below.

As can be better seen in FIG. 1B, outlet channel 106 has a bottom 122 below outlet 116 for guiding fluid below a fluid level, such as indicated by the dashed line 124. For each test channel 108, inlet 114 is elevated from outlet 116, which is in turn elevated from the fluid level 124 in outlet channel 106. As can be understood, inlet channel 104 can thus guide fluid at a fluid level above the fluid level in each test channel 108. A test channel 108 can hold fluid at a fluid level up to outlet 116, as indicated by the dashed line 126 in FIG. 1B, which is at a level above the fluid level 124 in outlet channel 106. As can be understood, back flow or diffusion through inlet 114 or outlet 116 can therefore be inhibited, thus limiting or eliminating cross-interference due to diffusion of molecules in the fluid from one test site to another test site.

A sample fluid may be diluted in dilution channel 110. Inlets 112 can be conveniently used to dilute the sample fluid multiple times. The number of inlets 112 may vary, for example, depending on the sample concentration and the desired amount of dilution. One of the inlets 112, such as inlet 112A may be adapted for connection to a sample source (not shown) and the other inlets such as 112B to 112D may be adapted for connection to a dilution solution source (not shown). Inlets 112 may also be connected to one or both of a substrate solution source and a washing solution source (not shown). Outlet channel 106 may be connected to a waste dispenser (not shown).

Substrate 102 can be made of a suitable material such as plastic, ceramic, graphite, glass, rubber, fabric, printed circuit board, silicon, suitable polymer, or the like. A combination of two or more of these materials may also be used. Substrate 102 can be prepared in a suitable manner known to persons skilled in the art.

Channels 104, 106, 108, and 110 can each has a width or depth on the order of 0.02 µm to 2000 µm, depending on the application. They can have different widths and depths. For example, inlet channel 104 can have a width of about 200 µm and a depth of about 50 µm; outlet channel 106 can have a width of about 300 µm and a depth of about 200 µm; and each test channel 108 can have a width of about 100 µm and a well depth of about 150 µm, wherein all depths are relative to the top surface of substrate 102. As can be appreciated, in this case, the liquid flow rate is faster in outlet channel 106 than in inlet channel 104, which can be advantageous because it reduces the chance for fluid to overflow from test channels 108 back into inlet channel 104. Channels 110 is shaped and sized for supplying a fluid to inlet channel 104 at a desired rate and for effectively diluting the fluid by a desired ratio. The size of channel 110 can be readily determined by a person skilled in the art for a given application.

Channels 104, 106, 108 and 110 may be formed using conventional microchip fabrication techniques including etching, embossing, molding, or the like. For example, a silicon mold can be fabricated using a soft-lithography method to make a master device and then a rubbery polymer (such as polydimethylsiloxane (PDMS)) substrate can be formed from the mold.

Channel surfaces may be coated with a polymeric, metallic, or ceramic material, or other materials if desired. In particular, the test site of each test channel 108 may have a surface, such as bottom surface 118, suitable for immobilizing molecules thereon. For example, for immobilizing antigens directly onto a bottom surface 118, the surface can be made of a plastic such as polyvinyl, polystyrene, or cellulose. Probe molecules (not shown) may be immobilized at the test site in each test channel 108. Probe molecules may be immobilized using a conventional immobilization technique, including physical adsorption, cross-linking, entrapment, covalent bonding, grafting, or a combination of the foregoing techniques. Probe molecules can be immobilized with a robotic nano- or pico-dispenser, or by introducing a fluid containing the probe molecules to test channels 108. The test channel surface may be coated with a surface that is suitable for selectively immobilizing probe molecules. For example, the surface may be coated with aminopropyltriethoxysilane (APTES). The coated surface may then be treated with a suitable cross-linker for capturing the probe molecules. For example, homo-bifunctional cross-linkers such as glutaraldehyde, or heterobifunctional cross-linkers such as 1-ethyl-3-(3-dimethylaminopropyl)carbodi-imide (EDC) may be applied to the APTES surface for selectively binding probe proteins. Immobilization of probe molecules can be optionally performed during use before detection. After probe immobilization, a thorough wash of the channels including the test channels can be conducted. The channel surfaces outside the test sites can be coated with blocking agents such as gelatin to eliminate non-specific binding of molecules to these surfaces. The washing and blocking can be conducted by automatic operation by connecting biochip 100 to a pumping system.

A cover (not shown), such as a transparent cover plate, may be provided on the top of substrate 102 to seal the channels and the test channels for flow-through operation. The cover can be made of a glass, plastic, or acrylic sheet. A film with one adhesive side may be used as the cover. The cover can prevent contamination during use. A transparent cover may allow detection of optical signals originated from the test channels 108.

Other components may be incorporated in or connected to biochip 100. For example, fluid sources (not shown) such as sample sources, substrate sources, washing fluid sources may be provided or linked to dilution channel 110, such as through one or more of inlets 112. In an alternative embodiment, some fluid sources may be connected directly to inlet channel 104, bypassing dilution channel 110. Fluid pumps (not shown) and valves (not shown) for controlling fluid flow in the channels and for supplying fluid to, or withdrawing fluid from, the channels may be provided. Electrical interconnects (not shown) and circuitry (not shown) may be provided for controlling the operation of biochip 100 and/or for measuring or detecting a signal such as an optical or electrical signal from the test sites in test channels 108.

In operation, a fluid, such as a sample fluid containing target molecules or a washing buffer solution, is introduced into test channels 108 through inlet channel 106 and inlets 116.

The sample fluid may be fed into dilution channel 110 through one of inlets 112, such as inlet 112A. Dilution fluids may be fed into dilution channel 110 through other inlets 112, such as inlets 112B to 112D, to dilute the sample fluid. The sample fluid can be diluted multiple times by introducing a dilution fluid at each one of a number of inlets 112. The dilution ratio at each inlet 112 can be individually controlled by adjusting the flow rates at inlets 112. The diluted sample fluid is received in inlet channel 104 and then in test channels 108. However, when dilution is not required or desired, a sample solution may be introduced into test channels 108 through inlet channel 104 without dilution.

Overflow of the fluid from the test channels 108 is received in outlet channel 106. The fluid levels in the inlet, outlet and test channels are maintained such that the fluid in test channels 108 is below inlet 114 and the fluid level in outlet channel 106 is below outlets 116. Therefore, back flow through inlet 114 and outlet 116 are inhibited. As can be appreciated, such fluid levels can be maintained conveniently when the fluid flows at a greater rate in outlet channel 106 than in inlet channel 104.

Different fluids may be introduced into each test channel 108 depending on the detection technique used. The fluids introduced may include probe solutions, sample solutions, washing solutions, substrate solutions, solutions containing labelling or signal generating molecules, and the like, as will be understood by persons skilled in the art. A continuous fluid flow may be maintained. Alternatively, fluid flow may be stopped for a certain period of time to allow certain interactions to occur, such as for incubation.

A molecule or molecular interaction is then detected at one, some or each of the test sites. The molecule detected can be a target molecule, or a signal generating molecule for indirect detection of the target molecule. The molecule or molecular interaction can be detected using various techniques, including conventional detection techniques for detecting molecules and molecular interactions. For example, the molecule or molecular interaction may be detected by detecting an optical, electrical, magnetic, radiation or electromagnetic signal indicative of the presence of the target molecule or occurrence of the molecular interaction. Example detection techniques include enzyme immunoassay (EIA) techniques. An EIA technique can be performed with an electrochemical detection technique (electrochemical EIA or EIA-EC) or with an optical detection technique. Possible EIA techniques include enzyme-linked immunosorbent assay (ELISA), direct EIA, competitive EIA, competitive inhibition EIA, sandwich EIA, and the like. These EIA techniques can be carried out in manners known to a person skilled in the art. In such techniques, the signal generating molecules can be product molecules produced from enzyme-catalysed reactions, which may be mobile in a fluid. The enzyme-catalyzed interaction or its product can be detected. For example, the interaction may generate heat, light, radiation, or sound. The reaction product may be electrochemically active or fluorescent. Detection of the enzyme-catalyzed interaction or its product can thus indicate the presence of the target molecules. For example, when the products are fluorescent, detection of fluorescent light from a test channel can indicate the presence of the target molecules in the sample solution. It can then be determined that the target molecules are present in the sample solution. The intensity of the fluorescent light can also indicate the concentration of the target molecules in the sample solution. Since back flow or diffusion is inhibited, cross-interference due to diffusion of these product molecules can be avoided or reduced.

The target molecule may be captured by probe molecules immobilized at the test site. Probe molecules may be pre-immobilized or immobilized during use. Different probe molecules may be immobilized at different test sites for detecting different target molecules.

For instance, probe proteins can be pre-immobilized on the bottom 118 of a test channel 108, thus defining the test site.

If the target protein allows for enzyme labelling, a direct EIA or ELISA detection may be conducted. In a direct EIA technique, the probe proteins can selectively capture target molecules, which are labelled with enzymes, in a sample fluid introduced into the test channels. A substrate fluid can be then introduced into the test channel. The substrates in the substrate fluid can produce detectable products in reactions catalysed by the enzymes attached to the target molecules at a test site. The higher the concentration of target molecules in the sample fluid, the more target molecules will be captured and thus producing a stronger signal.

In a competitive ELISA technique, the probe molecules can selectively capture a specific protein in a complex, which can contain either a target protein or an enzyme-conjugated competing protein. A sample fluid containing unknown concentrations of target molecules can be first introduced into a test channel 108. The target molecules are captured at some of the binding sites. A fluid containing known concentrations of competing proteins is then introduced into test channel 108. The competing proteins are captured at the remaining binding sites. By detecting how many competing proteins are captured, the presence or concentration of the target proteins can be indirectly detected.

In a competitive inhibition EIA technique, the probe molecules immobilized on the bottom surface of a test channel 108 can be the same type of molecules as the target molecules, such as the same antigens. During detection, both a sample fluid and a fluid containing enzyme-labelled molecules such as antibodies of a known concentration can be introduced into the test channel. An enzyme-labelled molecule can bind to either a target molecule or a probe molecule. There is thus competition between target molecules and probe molecules for binding with the enzyme-labelled molecules. Enzyme-labelled molecules attached to the target molecules cannot interact with the probe molecules. The presence of target molecules at the test site can inhibit a signal that would have resulted from interactions between enzyme-labelled molecules and probe molecules. Thus, the intensity of a detected signal can be inversely proportional to the concentration of the target molecules in the test channel. This technique can be particularly useful for detection of small proteins without a second epitope for enzyme labels.

In a sandwich-ELISA technique, the target protein may be captured by the probe protein. The test channels may be washed after introducing the sample fluid. Next, a fluid containing some other proteins labelled with enzymes may be introduced into the test channel to allow the other proteins to bind to the target proteins. After incubation, the test channels may be washed before conducting the ELISA detection. As can be appreciated, a capture target protein is sandwiched between two proteins, the probe protein and the enzyme-labelled protein.

The captured molecules or proteins including target molecules, such as antibodies or antigens, can be detected, for example, after introducing a fluid containing substrate molecules that can be converted by enzymatic reactions to coloured products for optical detection or electrochemically active products for the electrochemical detection.

As mentioned above, after a fluid is introduced into test channels 108, or after certain reactions are allowed to occur, the channels may be washed with a washing fluid, which may be fed into inlet channel 104 through dilution channel 110.

As can be appreciated by persons skilled in the art, samples containing same or different types of target molecules may be transported into different test channels 108 for simultaneous detection of multi-analytes when the different test channels 108 have different probe molecules immobilized therein.

In other techniques, the target molecules may be detected without an enzyme attached thereto. For example, the target molecules may be labeled with radioactive tracers and detected by sensing a radiation from each test channel 108. In yet other techniques, the target molecules may be detected without a label. For example, certain interaction of a specific molecule with another molecule may produce detectable heat or light.

In any event, advantageously, back diffusion can be inhibited or limited, and multiple sample tests can be simultaneously performed on biochip 100.

Further, biochip 100 can be conveniently used for analysis of both low and high concentration samples. For high concentration sample, the sample fluid can be conveniently diluted on biochip 100. Saturation in the test channels can be avoided even when the sample initially has very high concentrations of target molecules. Dilution can be carried out in multiple steps thus reducing the concentration at each step. As can be understood, when the dilution ratio is very high in a single dilution step, large errors can result. Thus, diluting at a low dilution ratio at each step can reduce the errors than may result from dilution. Dilution on biochip 100 can be carried out automatically.

Figure 2A:
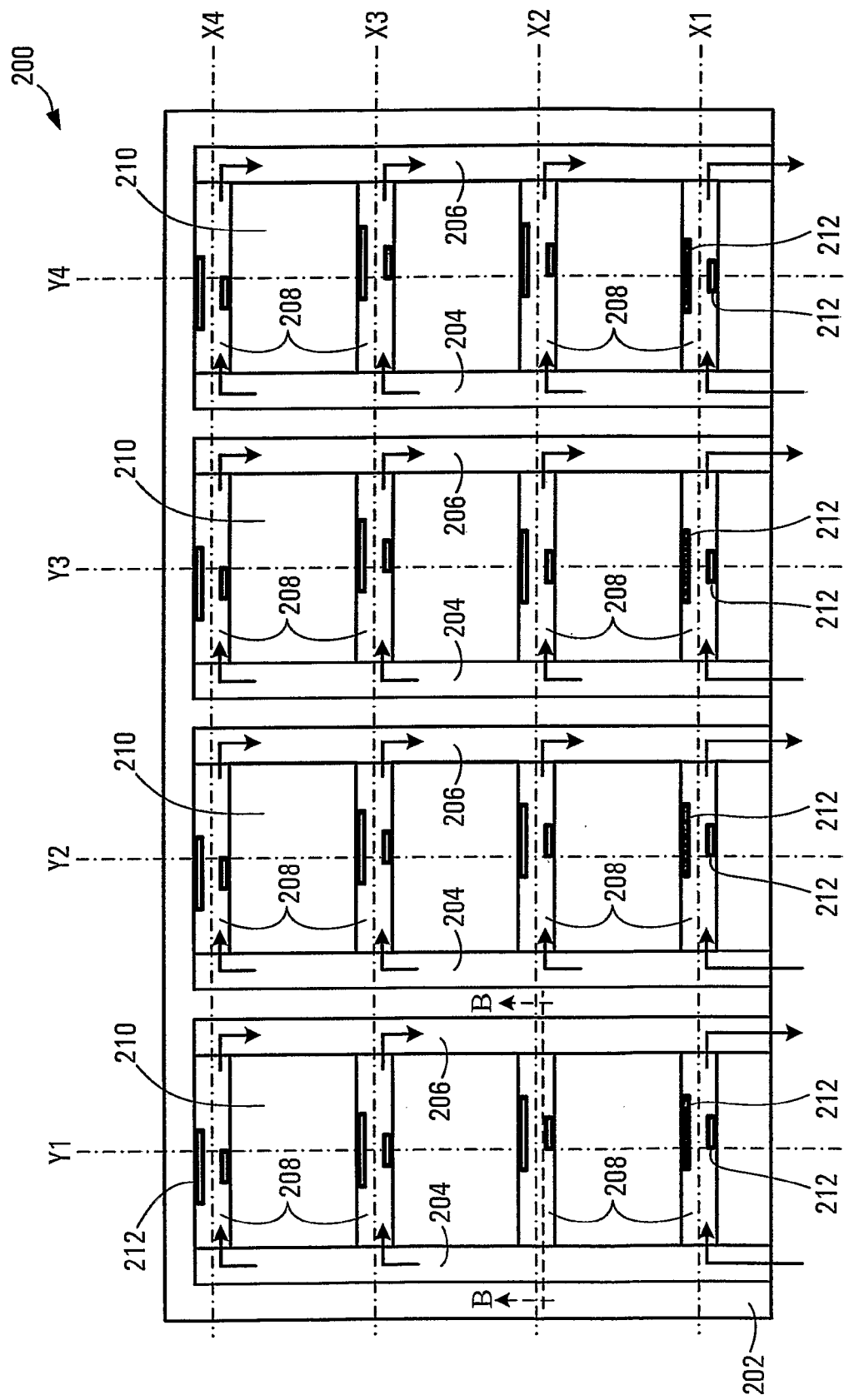
FIG. 2A is a plan view of another microchip exemplary of a further embodiment of the present invention.
Figure 2B:
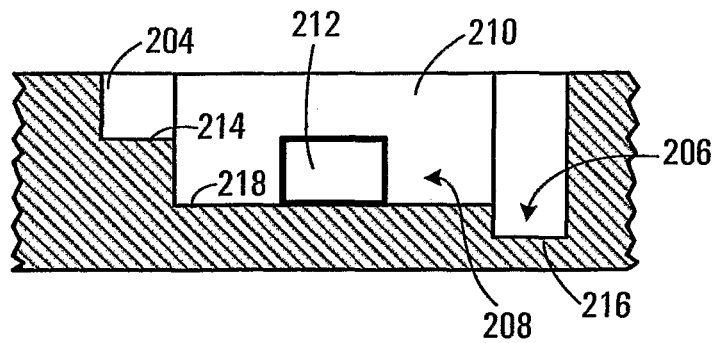
FIG. 2B is a partial cross-sectional view of the microchip of FIG. 2A taken along the line B-B.

FIGS. 2A and 2B illustrate a microfluidic biochip 200, exemplary of another embodiment of the present invention, which has an X-Y addressable array of test sites. Microchip or biochip 200 has a substrate 202 and inlet, outlet and test channels 204, 206, and 208 formed therein. Test channels 208 are arranged in rows and columns. Multiple columns of test channels 208 are formed in substrate 202. The number of test channels 208 may vary and can be selected depending on the particular application and manufacturing considerations. Each column of test channels 208 are separated into multiple rows by sidewalls 210 and share a common inlet channel 204 and a common outlet channel 206. Rows of test channels 208 in different columns are aligned for convenient addressing. One test site is formed in each test channel 208, which comprises a pair of electrodes 212, one of which is a working electrode and the other a counter or counter/reference electrode. As can be appreciated, counter electrodes may be replaced by reference electrodes. Alternatively, a reference electrode may be added in each test channel 208. As depicted, electrodes 212 are formed on the opposite sidewalls 210 within each test channel 208.

As can be better seen in FIG. 2B, each channel 204, 206 and 208 has a substantially flat bottom 214, 216 or 218. Bottom 214 is elevated from bottom 218, which is in turn elevated from bottom 216. Therefore, as with microchip 100, back diffusion from one test site to anther test site can be inhibited in microchip 200. The respective amount of elevation can be readily determined by persons skilled in the art depending on the application. For example, each elevation may vary between 25 and 100 μm. However, in an alternative embodiment, the channels may also be structured similar to that of microchip 100. In particular, a well may be formed in each test channels.

The detection of molecules or molecular interactions at each test site can be conducted using electrodes 212. As indicated in FIG. 2A by dot-dashed lines, the working electrodes 212 in each row and column can be respectively interconnected. The counter electrodes 212 in each row and column can be respectively interconnected. Each row of electrodes can have an X address, such as X1 to X4, and each column of electrodes can have a Y address, such as Y1 to Y4. Thus, the electrodes in each test channel can be addressed with an X-Y addressing technique. Conventional X-Y addressing techniques such as multiplexing techniques can be used. Such a technique can be readily implemented by a person skilled in the art. In microchip 200, electrical interconnections or I/O lines can be limited with simple multiplexing, as can be understood by a person of skill in the art.

The substrate and channels of microchip 200 may be formed as described above for microchip 100.

Electrodes 212 may be formed using any suitable technique including conventional techniques for forming electrodes. Electrodes 212 may have any suitable shape or size. Different electrodes may have different shapes and sizes or made of different materials. Working electrodes in different test channels may be spaced apart at distances on the order of 0.01 μm to 1000 μm, depending on the application and manufacturing limitations. Electrodes 212 may be made of a solid or porous material such as gold, silver, platinum, copper, titanium, chromium, aluminum, metal oxide, metal carbide, carbon, graphite, fullerene, conductive plastic, conductive polymer, metal impregnated polymers, or the like. A combination of two or more of these materials can be used.

Probe molecules (not shown) may be immobilized on working electrodes 212 or on bottoms 218 of test channels 208 proximate electrodes 212.

A cover (not shown), such as a transparent cover plate, may be optionally provided on the top of the substrate to cover the channels for sealing the flow-through channels.

Other components may be incorporated in or connected to biochip 200. For example, fluid sources (not shown) such as sample sources, substrate sources, washing solution sources may be provided or linked to input channel 204. Fluid pumps (not shown) and valves (not shown) for controlling fluid flow in the channels and for supplying fluids to the channels may be provided. Electrical interconnects (not shown) and circuitry (not shown) may be provided for biasing electrodes 212 and for measuring electrical signals such as voltages and currents at electrodes 212.

Biochip 200 may be operated in a similar manner as for biochip 100. Conveniently, an electrical signal can be sensed using electrodes 212 for detecting molecules or molecular interactions at each test site.

For example, the reaction products of the molecular interactions may comprise electrochemically active molecules. Each pair of electrodes 212 in a test channel 208 is biased to monitor the electrochemical reactivity at the test site in the test channel. As can be appreciated, when electrochemically active products are present in the liquid in the test channel, an electrical current can flow between the pair of electrodes 212.

As can be understood, in an EIA technique, a highly concentrated substrate solution can be used to produce a high concentration of electrochemically active products even when the target molecules have a very low concentration in the sample solution. Thus, such a technique can be highly sensitive. Alternatively, the product concentration can be significantly increased for high sensitivity detection by increasing the incubation time for the enzymatic reaction.

The amount of electrochemically active products produced at a test site can be detected by monitoring an electrical signal at electrodes 212, such as a current through an electrode 212. The concentration of the target molecules can be determined, for example, by comparing the detected current with a calibration curve of current vs. concentration, which can be obtained by measuring samples with known concentration of target molecules. In an amperimetric approach, the current due to generation of the electrochemically active products produced from the enzymatic reaction can be proportional to the concentration of the product, and can be approximately proportional to the target concentration in the sample solution.

As can be understood, as the test sites are separated by the sidewalls 210 and back flow from outlet channels 206 into test channels 208 and from test channels 208 into inlet channels 204 can be inhibited, diffusion of molecules from one test site to another can be limited or inhibited. In addition, when a liquid flow is maintained in the channels, upstream diffusion of molecules within test channels 208 is further limited. If the liquid can flow faster in outlet channel 206 than in inlet channel 208, backflow from outlet channel 206 into a test channel 208 can be further limited. As such, the chances of products produced at one test site moving to another test site can be reduced.

Figure 3A:
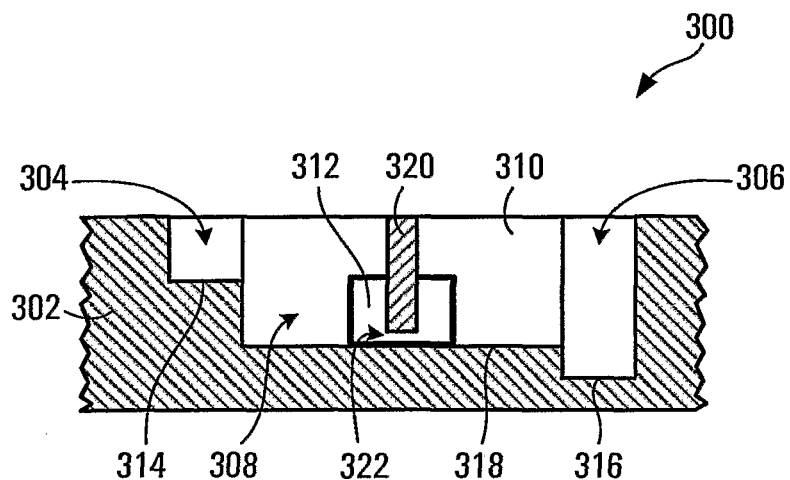
FIG. 3A is a partial cross-sectional view of a variation of the microchip of FIGS. 2A and 2B.
Figure 3B:
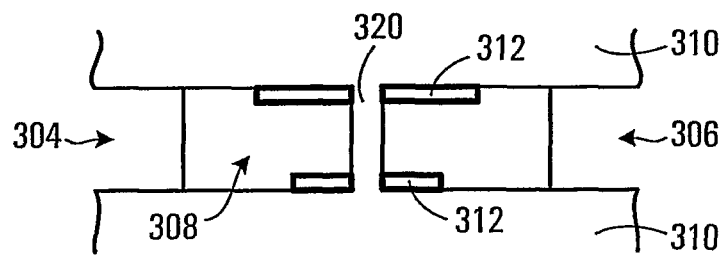
FIG. 3B is a partial plan view of the microchip of FIG. 3A.

To guide fluid towards electrodes 212, a section of each test channel 208 proximate the test site, i.e. electrodes 212, may be narrowed, as illustrated in FIGS. 3A and 3B.

FIGS. 3A and 3B illustrate a biochip 300 which is a variation of biochip 200. As in biochip 200, biochip 300 includes a substrate 302, and an inlet channel 304, an outlet channel 306, and a plurality of test channels 308 formed therein. Inlet channel 304 has a bottom surface 314. Outlet channel 306 has a bottom surface 316. Test channels 308 are defined by sidewalls 310 and bottom surface 318.

Biochip 300 has a panel 320 extending between sidewalls 310 and elevated from bottom surface 318, thus defining an opening 322 to allow the liquid to flow through. The narrowed section at opening 322 guides fluid towards the test site for effective contact with electrodes 212 or a surface having probe molecules immobilized thereon. Panel 320 can also further prevent backflow. Panel 320 may be shifted vertically to vary opening 322 for controlling the flow rate.

Figure 4:
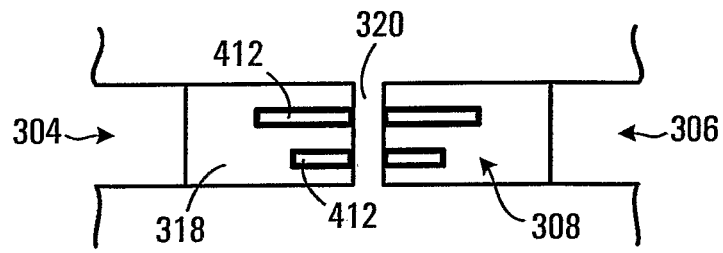
FIG. 4 is a partial plan view of a variation of the microchip of FIG. 3A.

Electrodes 212 may be disposed in a test channel differently than as shown in FIGS. 3A and 3B. For example, as illustrated in FIG. 4, electrodes, such as electrodes 412, can be formed on bottoms 318 of test channels 308. A pair of working and counter/reference electrodes 412 may be disposed at bottom 318 adjacent opposite sidewalls, as depicted.

As discussed above, probe molecules can be immobilized on a surface in a test channel. Probe molecules may include antibodies, antigens, peptides, aptomers, DNAs, and the like, which can specifically capture and bind to the target molecules. Probe molecules can capture target molecules contained in a sample solution introduced into the test channels. The sample solution may be flown through each test channel to allow the target molecules and/or enzyme-labelled molecules (reporter molecules) to be captured by the probe molecules. The reporter molecules in a competition detection scheme are labelled with enzyme molecules. A reporter molecule can be an antibody, antigen or any molecule with affinity to the probe molecule. The target molecules may be directly labelled before they react with the probe molecules. In each of the above steps, a liquid may be flown through the channels to attach a next molecule to the already immobilized molecule. To ensure accuracy and efficiency, the channels may be washed with a washing solution before feeding the next liquid. In particular, the channels may be washed before providing substrate solutions to the test channels to ensure that mobile enzymes are removed from the test channels.

Figure 5A:
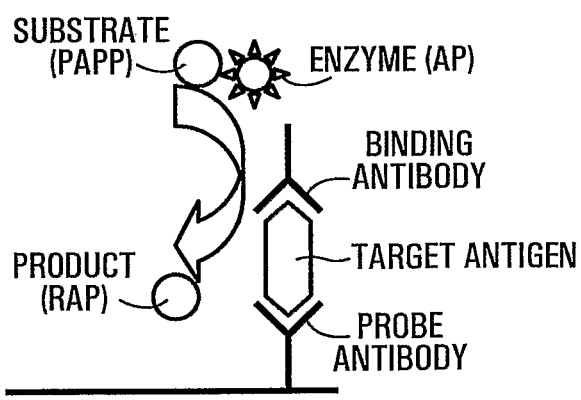
FIGS. 5A and 5B are schematic diagrams illustrating exemplary enzyme immunoassay techniques.

A specific example of a sandwich immunoassay technique is illustrated in FIG. 5A. A probe antibody is immobilized on the surface of a working electrode or surface close to the working electrode. The target molecule is an antigen of interest and is bond to the probe antibody. An enzyme (such as ALP)-labelled second antibody is transported to bind to the target antigen after washing. Then the substrate, such as a PAPP including dephosphorylase-PAPP, is delivered into the detection spots for an enzymatic reaction, for example by flowing a substrate solution through the test channels. The substrate molecule reacts under enzyme catalysis at the enzyme active site to produce an electrochemically active product, PAP. Advantageously, PAP can be detected electrochemically when the electrodes are biased to a low potential such as 300 mv with reference to an Ag/Ag reference electrode.

Figure 5B:
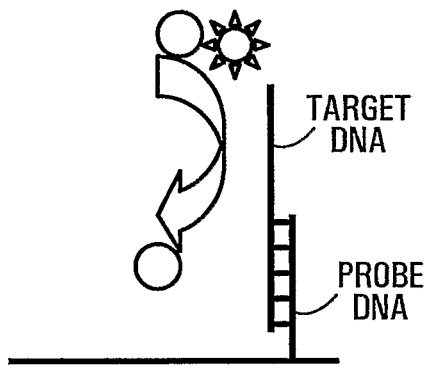

Similarly, in the example shown in FIG. 5B, a probe DNA is first immobilized on the electrode surface. The target DNA is then bond to the probe DNA. The target DNA is labelled with an ALP enzyme. The enzyme can catalyse conversion of PAPP substrates to PAP products as in FIG. 5A for electrochemical detection.

Figure 6A:
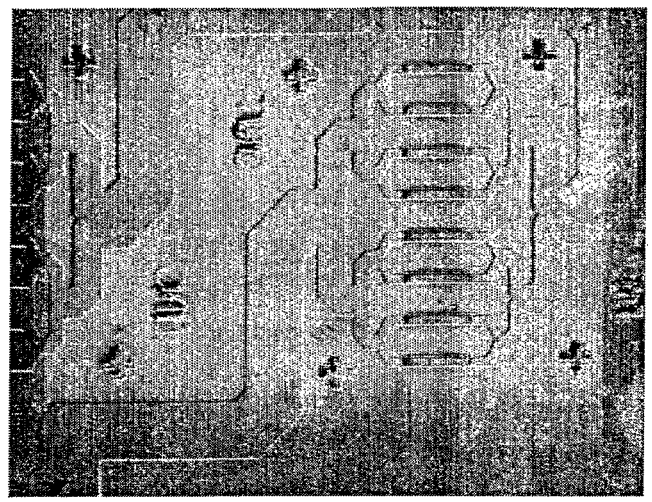
FIG. 6A is a partial image of a mold for forming a microchip.

FIG. 6A shows a partial image of a silicon mold for forming a biochip exemplary of embodiments of the present invention. The mold was prepared with a soft-lithography method. The test channels (seen as parallel narrow channels) have widths of about 100 μm.

Figure 6B:
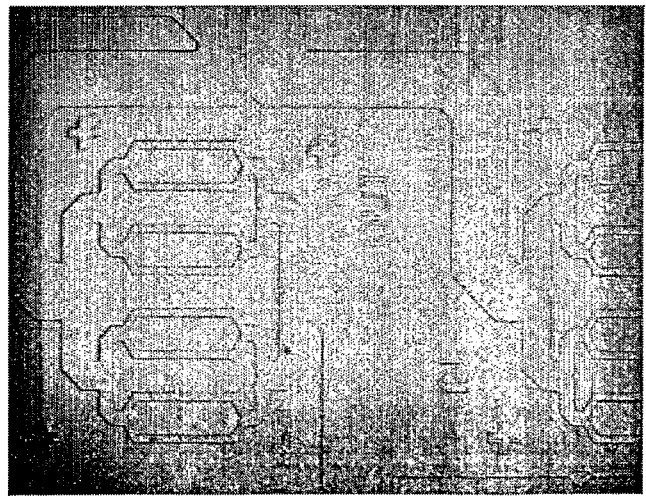
FIG. 6B is a partial image of a microchip formed from the mold of FIG. 6A.

FIG. 6B shows a partial image of a biochip formed from the mold shown in FIG. 6A. The biochip was formed by pouring a rubbery polymer (PDMS) over the mold, curing the polymer, and then separating the cured polymer from the mold. The biochip is suitable for ELISA analysis or detection. Probe antigens were immobilized in the test channels. A transparent polyacrylic sheet was attached to the biochip as the cover for sealing the device.

To test biochips such as the one shown in FIG. 6B, target proteins were immobilized as follows on the biochips. A thin aminopropyltriethoxysilane (APTES) film was coated or grafted on the PDMS surface of the test channels. The APTES surface was treated with homo-bifunctional cross-linkers (glutaraldehyde) for capturing immunoglobulin proteins on the APTES film. Alternatively, succinic acid anhydride generated carboxyl groups were applied onto the APTES surface, and heterobifunctional cross-linkers (1-ethyl-3-(3-dimethylaminopropyl)carbodi-imide (EDC)) were then applied to the surface to covalently bind proteins onto the PDMS-APTES surface through the carboxyl groups.

A PDMS-APTES surface can be prepared by first cleaning the PDMS surface and then immersing the surface in an ethanol solution containing about 10% v/v APTES for about 10 minutes at room temperature. The APTES treated PDMS is rinsed with 96% ethanol, followed by air-drying, and then heated at 80° C. in a vacuum oven for about 2 hours.

Covalent immobilization can be realized via EDC as follows. Succinic acid, anhydride (SAA) can be first used to modify the APTES surface by immersing the PDMS-APTES surface in a 50 g/ml SAA solution for about 2 hours at room temperature. The pH value of the solution is adjusted by using a 3M NaOH solution to keep the solution stable at pH 6.0. Then surface is rinsed by phosphate-citrate buffer and dried under nitrogen flow. EDC and protein mixture are dropped onto the modified solid surface for cross-linking. The concentration of the EDC is 20 μg/ml. The reaction buffer has 0.01M of phosphate-citrate, with a pH of 4.6. The cross-linking process lasts for about 1 hour at room temperature. The cross-linking process is terminated by immersing the surface in a Tris-HCl buffer. The protein coated surface is then immersed in a 1% bovine serum albumin (BSA) for blocking unoccupied surface for about 2 hours at about 37° C. or for about 8 hours at room temperature.

Covalent immobilization can also be realized via glutaraldehyde (GA) as follows. The APTES treated PDMS surface is modified by GA to covalently immobilize protein on the PDMS surface. The amino groups on the surface are activated by 2.5% GA for 1 hour at room temperature. The surface is rinsed with a pH 8.0 Tris-HCl buffer, and dried with nitrogen gas. Protein probes in Tris-HCl are added onto the glutaraldehyde-activated surface. The cross-linking reaction can take place at room temperature for about 2 hour. After washing, the protein-coated surface is surface-blocked with the block reagent described above.

Example biochips fabricated as above have shown good performance. For example, rabbit IgG were immobilized in the test channels as described in the preceding paragraph. Sample solutions containing varying concentrations of enzymes labeled with anti-rabbit IgG were flown through the channels and test channels to immobilize the enzymes in the test channels by antibody-antigen binding. After feeding each sample solution, the channels and test channels was washed with a washing solution. A substrate solution was then flown through the test channels. Fluorescent light emitted from the test channels was detected. The intensities of the fluorescent light were substantially linearly dependent on the concentration of the sample solutions. The linear dependence indicates that cross-interference between test channels was very low. It has been found that as low as about 5.6 pg/ml of enzyme concentration can be detected.

Exemplary embodiments disclosed herein are useful for detecting low level of antigens, antibodies, peptides, DNA, proteins and other biomolecules in fluid or tissue samples. Low levels of DNA, RNA and other biomolecules such as glucose, which can be enzymatically converted to electrochemically active species, can be detected using embodiments of the present invention. Embodiments of the present invention can be incorporated into existing optical detection systems based on enzyme-catalyzed bio-reactions, in which PCR amplification can be eliminated. The exemplary biochips disclosed herein may provide a basic platform for a variety of applications, for example in diagnostics, drug discovery, target validation and pathogen detection.

Embodiments of the invention can be used in competition and displacement immunoassays where target antigens are labeled with enzymes for competition binding or displacement for detection. Radioactive tracers can be used to label the target molecules or binding molecules as reporters. The sandwich immunoassay is suitable for use with high molecular weight antigens, which possess at least two antigenic determinants or epitopes, but the competition and displacement immunoassay can be used to detect different antigens.

As can be appreciated, the operation of the biochips described herein can be automated. The biochips can be connected to utility modules. The operation of a biochip can be controlled by a computer or a microprocessor. The liquid flow rate and flow time can be conveniently adjusted.

As the substrate solution can continuously flow through the test sites generating more and more product molecules, even a low concentration of target molecules in the analyte solution can be detected. The substrate solution can also have a high concentration of substrate molecules. The liquid flow rate and flow time can be conveniently adjusted to control the enzyme reaction, for example, for achieving different detection sensitivities.

As can be appreciated, target molecules can be immobilized or labelled in other suitable manners. For example, the surface of an electrode may have a coating that can selectively capture the target molecules. In a further example, when the target molecule is itself an enzyme, it may not be necessary to attach another enzyme to it.

As can be understood, the enzyme reactions or target molecules present at different test sites can be identified using electrode addressing techniques including conventional addressing techniques. For example, the test sites may form an array of rows and columns and X-Y addressing techniques may be used.

Advantageously, high-density array biochips disclosed herein can be made compact without creating substantial cross-interference for a flow-through system. It can also be fabricated inexpensively and easily, for example, using inexpensive and matured printed circuit board technology to fabricate a plastic based microarray chip with microchannels, or embossing fabrication process.

As can be appreciated, working and counter or reference electrodes 212 may be interchangeable. In alternative embodiments, separate counter and reference electrodes, thus more than two electrodes, can be provided in each test channel 208. The reference electrodes can be interconnected with each other. The implementation and operation of electrodes for detecting electrochemical reactions including the use of reference electrodes can be readily understood by persons skilled in the art.

Embodiments of the invention may also be useful in protein expression profiling. Measurement of the variation in the expression of known proteins within tissues or cells over time, or in response to challenge by drugs, toxins, injury or disease, may require high throughput operation and can be conveniently performed using embodiments of the present invention.

Embodiments of the invention can be used in high density array-sensors with high sensitivity and specificity. Accuracy and reliability of the embodiments disclosed herein can be high because cross-interference due to diffusion can be inhibited or limited. It is also convenient to perform multifold dilution of sample, automatic post-immobilization probe treatment, and washing.

Advantageously, array dispensers are not necessary for operating biochips disclosed herein. Total assay time can be reduced compared to conventional biochips. The requirement of the samples amount is significantly decreased.

Other features, benefits and advantages of the present invention not expressly mentioned above can be understood from this description and the drawings by those skilled in the art.

The above described embodiments are intended to be illustrative only and in no way limiting. The described embodiments are susceptible to many modifications of form, arrangement of parts, details and order of operation. The invention, rather, is intended to encompass all such modification within its scope, as defined by the claims.

What is claimed is:

1. A microchip comprising:
   a substrate;
   an inlet channel in said substrate;
   an outlet channel in said substrate for guiding fluid below a fluid level in said outlet channel;
   a plurality of test channels in said substrate formed between said inlet channel and said outlet channel, for guiding fluid flow from said inlet channel to said outlet channel, each one of said test channels having an inlet connected with said inlet channel and an outlet connected with said outlet channel, said inlet elevated from said outlet for inhibiting back flow through said inlet, said outlet elevated from said fluid level for inhibiting back flow through said outlet; and
   one test site in each one of said test channels, for detection of at least one specific molecule and a molecular interaction at said test site;
   wherein each one of said inlet channel, said outlet channel, and said test channels has a substantially flat bottom, said bottom of said inlet channel elevated from said bottoms of said test channels, said bottoms of said test channels elevated from said bottom of said outlet channel and elevated from said fluid level in said outlet channel;
   wherein at least one of said test channels comprises a well for holding fluid therein; and
   wherein at least one of said test channels comprises an overflow wall for forming said well, said overflow wall defining the outlet of said at least one of said test channels.

2. The microchip of claim 1, wherein said inlet channel and said outlet channel are adapted to allow a liquid to flow at a greater rate in said outlet channel than in said inlet channel.

3. The microchip of claim 1, wherein each one of said test sites comprises a surface suitable for immobilizing specific molecules thereon.

4. The microchip of claim 1, further comprising probe molecules immobilized at each one of said test sites, said probe molecules having specific affinity to selected target molecules.

5. The microchip of claim 4, wherein different probe molecules are immobilized at different ones of said test sites for detecting different target molecules.

6. The microchip of claim 1, further comprising a plurality of electrodes, one of said electrodes at each one of said test sites.

7. The microchip of claim 6, wherein at least one of said test channels comprises a narrowed section proximate said test site in said at least one test channel for guiding fluid towards said test site.

8. The microchip of claim 6, wherein said plurality of electrodes are first electrodes, said microchip further comprising a plurality of second electrodes, one of said second electrodes in each one of said test channels.

9. The microchip of claim 8, wherein said first electrodes are interconnected and said second electrodes are interconnected, such that each pair of said electrodes in each one of said test channels is uniquely addressable.

10. The microchip of claim 8, further comprising probe molecules immobilized proximate said first electrodes.

11. The microchip of claim 1, wherein said test channels extend substantially in parallel.

12. The microchip of claim 1, further comprising a dilution channel formed in said substrate, said dilution channel in fluid communication with said inlet channel and having a first inlet for reception of a first fluid and at least one second inlet for reception of a second fluid to dilute said first fluid.

13. The microchip of claim 12, wherein said at least one second inlet comprises a plurality of second inlets.

14. The microchip of claim 1, wherein said substrate comprises polydimethylsiloxane (PDMS).

15. The microchip of claim 14, wherein a PDMS surface in each one of at least one of said test sites is coated with aminopropyltriethoxysilane (APTES), thus forming a PDMS-APTES surface.

16. The microchip of claim 15, wherein probe molecules are covalently immobilized on said PDMS-APTES surface through cross-linkers.

17. The microchip of claim 16, wherein said cross-linkers comprise at least one of glutaraldehyde and 1-ethyl-3-(3-dimethylaminopropyl)carbodi-imide.

18. The microchip of claim 1, wherein at least one of said inlet channel, said outlet channel and said test channels is adapted for connection to at least one of a pump and a valve for regulating fluid flow.

19. The microchip of claim 1, further comprising at least one fluid in said inlet channel, said outlet channel, and said test channels, wherein fluid level in each of said test channels does not exceed fluid level in said inlet channel.

20. The microchip of claim 19, wherein the fluid level in said outlet channel does not exceed the fluid level at the outlet of each of said test channels.

* * * * *